(12) United States Patent
Purkins et al.

(10) Patent No.: US 8,740,014 B2
(45) Date of Patent: Jun. 3, 2014

(54) DOSE COUNTER FOR DISPENSERS

(75) Inventors: Graham R. Purkins, Loughborough (GB); Lee A. Kristensen, Ipswich (GB); Sarah Jones, Olney (GB); David J. Greenleaf, Loughborough (GB)

(73) Assignee: 3M Innovative Properties Company, St. Paul, MN (US)

( * ) Notice: Subject to any disclaimer, the term of this patent is extended or adjusted under 35 U.S.C. 154(b) by 1200 days.

(21) Appl. No.: 10/596,325

(22) PCT Filed: Nov. 30, 2004

(86) PCT No.: PCT/US2004/039926
§ 371 (c)(1),
(2), (4) Date: Jun. 29, 2007

(87) PCT Pub. No.: WO2005/060535
PCT Pub. Date: Jul. 7, 2005

(65) Prior Publication Data
US 2007/0246042 A1 Oct. 25, 2007

(30) Foreign Application Priority Data
Dec. 10, 2003 (GB) .................................. 0328635.8

(51) Int. Cl.
*B67D 7/22* (2010.01)
*A61M 15/00* (2006.01)

(52) U.S. Cl.
CPC .......... *A61M 15/0065* (2013.01); *A61M 15/009* (2013.01); *A61M 2015/0068* (2013.01)
USPC ........................................ 222/36; 128/205.23

(58) Field of Classification Search
CPC .......................... A61M 15/0065; A61M 15/009
USPC ................. 222/30, 36, 38, 321.6, 321.9, 162; 128/205.23, 200, 23, 200.22; 215/230; 116/318
See application file for complete search history.

(56) References Cited

U.S. PATENT DOCUMENTS 3,655,952 A * 4/1972 Johnson et al. ............. 235/94 R
4,565,302 A 1/1986 Pfeiffer et al.
(Continued)

FOREIGN PATENT DOCUMENTS

EP 0 269 496 A2 1/1988
FR 2854878 A1 11/2004
(Continued)

*Primary Examiner* — Lien Ngo

(57) ABSTRACT

A dose counter for use with an inhaler comprising a container for medicament equipped with a reciprocal actuation means to dispense a dose of medicament therefrom, the dose counter comprising: a fixed ratchet member, a trigger member constructed and arranged to undergo reciprocal movement coordinated with the reciprocal movement between the actuation means and the container, said reciprocal movement comprising an outward stroke and a return stroke, a counter member constructed and arranged to undergo a predetermined counting movement each time a dose is dispensed, the counter member being biased towards the ratchet and trigger members and being capable of counting motion in a direction generally orthogonal to the direction of reciprocal movement of the trigger member, the counter member comprising: a first region for interaction with the trigger member which comprises at least one inclined surface which is engaged by the trigger member during its outward stroke causing the counter member to undergo counting motion, and a second region for interaction with the ratchet member which comprises at least one inclined surface which is engaged by the ratchet member during the return stroke of the trigger member causing the counter member to undergo further counting motion to complete said predetermined counting movement.

12 Claims, 8 Drawing Sheets

(56) References Cited

U.S. PATENT DOCUMENTS

| | | |
|---|---|---|
| 5,174,473 A | 12/1992 | Marelli |
| 5,289,946 A | 3/1994 | Fuchs |
| 5,611,444 A | 3/1997 | Garby et al. |
| 5,799,651 A | 9/1998 | Garby et al. |
| 5,988,496 A | 11/1999 | Bruna |
| 6,164,494 A | 12/2000 | Marelli |
| 6,234,168 B1 | 5/2001 | Bruna |
| 6,283,365 B1 | 9/2001 | Bason |
| 6,446,627 B1 | 9/2002 | Bowman et al. |
| 7,195,134 B2 * | 3/2007 | Ouyang et al. ............ 222/36 |
| 7,232,043 B2 * | 6/2007 | Wong et al. ............... 222/38 |
| 7,407,066 B2 * | 8/2008 | Ouyang et al. ............ 222/36 |
| 2007/0051745 A1 * | 3/2007 | Poulard ..................... 222/36 |
| 2009/0054851 A1 * | 2/2009 | Radmer et al. ............ 604/211 |

FOREIGN PATENT DOCUMENTS

| | | |
|---|---|---|
| WO | WO 95/08484 | 3/1995 |
| WO | WO 96/39337 | 12/1996 |
| WO | WO 98/56444 | 12/1998 |
| WO | WO 98/56445 | 12/1998 |
| WO | WO 98/56446 | 12/1998 |
| WO | WO 99/36115 | 7/1999 |
| WO | WO 00/59806 | 10/2000 |
| WO | WO 02/069252 | 9/2002 |
| WO | WO 02/069253 | 9/2002 |
| WO | WO 03/080162 | 10/2003 |
| WO | WO 2004/026380 | 4/2004 |
| WO | WO 2005/007226 | 1/2005 |
| WO | WO 2005/041850 | 5/2005 |
| WO | WO 2005/113044 | 12/2005 |

* cited by examiner

DOSE COUNTER FOR DISPENSERS

CROSS REFERENCE TO RELATED APPLICATIONS

This application is a national stage filing under 35 U.S.C. 371 of PCT/US2004/039926, filed Nov. 30, 2004, which claims priority to United Kingdom Application No. 0328635.8, filed Dec. 10, 2003, the disclosure of which is incorporated by reference in its/their entirety herein.

This invention relates to dose counters for dispensers and in particular to dose counters for use with an inhaler comprising a container for medicament equipped with a reciprocal actuation means, such as a valve, more particularly a metering valve having a valve stem, to dispense a dose of medicament from the container.

Since the metered dose pressurised inhaler was introduced in the mid-1950's, inhalation has become a widely used route for delivering bronchodilator drugs and steroids to the airways of asthmatic patients. More recently, inhalation from a pressurised inhaler has been a route selected for administration of other drugs which are not primarily concerned with treatment of a bronchial malady.

A metered dose inhaler generally comprises a container equipped with a metered dose dispensing valve. The container contains a pressurised aerosol formulation which generally comprises a liquefied propellant, a surfactant, a medicament and optionally a solvent. The medicament may be in the form of a dispersion or in solution in the aerosol formulation. Metered dose dispensing valves generally comprise a valve stem which is moved inwardly with respect to the container to dispense a metered dose of aerosol formulation. The metering chamber of the valve is normally open to receive contents from the container when the valve is in its rest position although some designs of valve may only open the metering chamber as the valve stem is returned or when it is depressed to fire. The valve stem is generally biased to its rest position by means of a return spring.

Basic metered dose inhalers, normally referred to as press-and-breathe inhalers, comprise a generally cylindrical housing, a mouthpiece and a nozzle block contained within the housing. The aerosol container is inserted within the housing with the valve stem in the nozzle block. In use, a patient places their lips over the mouthpiece and presses the base of the aerosol container causing the container to move relative to the valve stem to fire a dose of medicament through the mouthpiece.

More sophisticated types of inhaler automatically fire the aerosol in response to inhalation. Such devices generally comprise a mechanism that can apply a firing force to the aerosol container with a trigger mechanism which prevents the firing force from acting on the container until inhalation is detected through the mouthpiece.

One of the disadvantages arising from the use of such known inhalers is that the patient cannot readily determine the amount of medicament in the container at any given time. In an extreme case this could mean that the patient in need of a dose of medicament will find that the inhaler will not dispense a dose because its contents have already been exhausted. There have been numerous proposals for dose counters to be used with pressurised aerosol inhalers. It has proved to be difficult to produce such a dose counter which is both economic and reliable. One of the problems associated with such dose counters is that they should count a single dose only when a dose of medicament has been dispensed. Thus, the count should not be triggered if the valve stem is not sufficiently depressed to fire the valve and it should not count more than one dose during a firing cycle e.g. if the return cycle of the valve is interrupted. Furthermore, the counter must be sufficiently sturdy so that it will not alter the count when the inhaler is subject to the rigors of being carried in a pocket, bag etc. Furthermore, the counter must have a sufficient life to withstand the number of doses to be dispensed from the aerosol container. Furthermore, the dose counter must be able to compensate for the normal manufacturing variation in the production of the inhalers which may result in a slightly different length of travel of the valve stem before the valve is triggered.

Various designs of dose counter have been proposed in which a counter ring or indexing mechanism is advanced in two stages; a first counting motion occurring during the relative motion between the container and the valve stem to dispense the medicament and a second counting motion occurring when the inhaler is returned to its rest position. Examples of such designs are disclosed in WO98/56444, WO98/56445, WO98/56446, WO00/59806, WO02/69252, WO02/69253, EP269496, EP949584 and U.S. Pat. No. 5,611,444.

U.S. Pat. No. 4,565,302 discloses a dosing mechanism in the form of a manually operated, single-acting piston pump which dispenses a metered dose of substance e.g. in atomised form, during each activating stroke, which dosing mechanism comprises a counter. A counting ring which is fixed so that it cannot move in the axial direction of the actuating stroke is mounted for rotary motion on a base part of the dosing mechanism and is advanced during the actuating stroke by an indexing device. The indexing device and counting ring have correspondingly bevelled ribs which co-operate during the actuating stroke to rotate the counting ring. The counting ring may be provided with a safety catch which comprises a notched star-shaped portion in the form of external teeth on the base which co-operate with resilient plastic strips projecting inwardly from the counting ring. The plastic strips co-operate with the notched star in the manner of pawls. As a result of the shape of the teeth which comprise relatively shallow sloping tooth profiles with an asymmetric notch in the tooth gullet it is assured that the plastic strips automatically rotate the counting ring to complete a count. The safety catch also prevents backward rotation of the counting ring.

The present invention provides an alternative construction of dose counter which is particularly suitable for use with pressurised aerosol inhalers.

According to the invention there is provided a dose counter for use with an inhaler comprising a container for medicament equipped with a reciprocal actuation means to dispense a dose of medicament therefrom, the dose counter comprising:

a fixed ratchet member, a trigger member constructed and arranged to undergo reciprocal movement coordinated with the reciprocal movement between the actuation means and the container, said reciprocal movement comprising an outward stroke and a return stroke, a counter member constructed and arranged to undergo a predetermined counting movement each time a dose is dispensed, the counter member being biased towards the ratchet and trigger members and being capable of counting motion in a direction generally orthogonal to the direction of reciprocal movement of the trigger member, the counter member comprising:

a first region for interaction with the trigger member which comprises at least one inclined surface which is engaged by the trigger member during its outward stroke causing the counter member to undergo counting motion, a second region for interaction with the ratchet member which comprises at least one inclined surface which is engaged by the ratchet member during the return stroke of the trigger member causing the counter member to undergo further counting motion to complete said predetermined counting movement.

The counter mechanism of the invention is designed to allow precise counting by advancing the counter member, which is normally in the form of a counter ring, partly on the outward stroke of the trigger and partly on the return stroke. In the case of a conventional inhaler, the outward stroke of the trigger will correspond to the depression of the valve stem within the container causing firing of the valve and the return stroke of the trigger will correspond to the return of the valve stem to its rest position under the influence of its return spring, allowing metering of the next dose. However, the invention is equally applicable to other reciprocal actuators e.g. a valve with a stem that when depressed within the container both meters the contents and fires or a valve which both meters the contents and fires upon an outward movement of the valve stem from the container.

The counter member may conveniently be resiliently biased for example by a coil spring or leaf spring towards the ratchet member and trigger member.

The dose counter is preferably constructed and arranged such that the counter member is urged to return to its previous count position if the outward stroke of the trigger is interrupted and reversed. The device is preferably constructed and arranged such that if the return stroke of the trigger is interrupted and reversed the counter member will return to its position at the end of the previous outward stroke of the trigger.

Some allowance for lost motion is inherent in the construction of the dose counter due to the counter member being resiliently biased towards the ratchet and trigger members. Additional allowance for lost motion may be achieved by constructing and arranging the dose counter such that the trigger member disengages from the counter member during the return stroke. Allowance for lost motion through resiliently biasing of the counter member and/or the aforesaid disengagement of the trigger member allows the counter mechanism to accommodate movement of the reciprocal (e.g. a valve stem of an) actuation means and hence the trigger well beyond that required to dispense the dose and advance the counter without causing the counter to miscount.

The dose counter does not require delicate parts that easily break or distort and may be constructed of robust parts that may readily be fabricated from plastics material.

In preferred embodiments, the counter member of the dose counter is in the form of a ring. The ring may be open or closed, but typically it is closed. In the following it is understood that under the term counter member, a counter ring is preferred. The counter member is typically mounted for rotation within a housing and has markings e.g. integers or color-coded markings, on the cylindrical side surface which may be viewed through a window in the housing to determine the count. In the direction of advancing count on the counter member, the aforesaid markings may show a count up and/or a count down of the number of doses. The counter member comprises a first region for interaction with the trigger and a second region for interacting with the ratchet member. Each region typically comprises a series of inclined surfaces that defines a series of teeth. In one embodiment of the invention the counter member comprises a first set of teeth for engagement with the trigger and a second set of teeth for engagement with the ratchet member. In a second embodiment of the invention the counter member comprises one set of teeth for engagement by both the trigger and ratchet member.

The ratchet member, which is fixed e.g. relative to the counter member and/or the trigger member of the dose counter, may comprise at least one projection or tooth. The ratchet member may be fixed (directly or indirectly) e.g. to a housing of the dose counter and/or may be conveniently formed in the dose counter housing, e.g. as a projection or tooth projecting downwardly from the housing lid. Alternatively, depending on the particular reciprocal actuation means and/or inhaler being used, the ratchet member may be secured (directly or indirectly) to and/or formed in the housing of the inhaler and/or to the container. A plurality of ratchet members may be circumferentially spaced to co-ordinate with teeth on the counter member.

The trigger member, which is arranged to undergo reciprocal movement coordinated with the reciprocal movement between the actuator (e.g. valve) and the container, may be (directly or indirectly) secured to the valve ferrule and/or container and/or the valve stem of a valve depending on the particular reciprocal actuation means and/or inhaler being used. In some cases, for example in a shuttle valve where the container is held fixed and the valve stem is being moved, the trigger member could even be a part of the valve stem. For example in the case of a conventional press-and-breath-inhaler, in which the container is typically positioned vertically with the valve stem oriented downwards and located in a nozzle block and the inhaler is actuated by moving the container downwardly, the trigger may be secured to the ferrule and/or container, so that the trigger moves therewith when the container is depressed to fire the valve and released to return to its rest position under the influence of the valve spring. Alternatively the trigger may be secured directly/indirectly to the inhaler housing and the remainder of the dose counter secured to the ferrule and/or container. The trigger may comprise one or more teeth for engagement with the surfaces of the teeth of the counter member. Thus, for a conventional press-and-breath inhaler with the trigger mounted directly/indirectly to the valve ferrule and/or the container, as the aerosol container is depressed, the trigger during its outward stroke will typically move downwardly and engage upwardly facing teeth of the counter member and when the aerosol container is released to return to its rest position under the influence of the return spring of the valve, the trigger during its return stroke will move upwardly away from, typically, eventually disengaging, the teeth of the counter member.

The counter member is resiliently biased towards the fixed ratchet member and trigger member, i.e. for conventional press-and-breath inhalers with the trigger member mounted directly/indirectly to the valve ferrule and or the container, the counter member is typically biased upwardly. The counter member may conveniently be biased by a coil spring or leaf spring, e.g. for conventional inhalers acting on the bottom of the counter member.

In the rest position of the inhaler, the counter member is desirably resiliently biased in contact with the ratchet member. More desirably for those embodiments including a counter member having teeth, the ratchet member is fully engaged in the tooth gullet of a tooth on the counter member. This contact and/or engagement facilitate the prevention of rotational motion of the counter member (e.g. counter ring) in either direction.

In preferred embodiments of the invention the tooth gullet on the counter member (e.g. counter ring) is defined between two inclined surfaces defining an obtuse, 90° or between an inclined surface and a vertical surface defining an acute angle (in direction of advancing count on the counter member the inclined surface is followed by the vertical surface (i.e. the inclined surface is on the non-counting side while the vertical surface is on the counting side of the tooth gullet), or between a horizontal surface and a vertical surface (in direction of advancing count on the counter member the horizontal surface (on the non-counting side) is followed by the vertical surface (on the counting side of the tooth gullet)); or between a horizontal surface and an inclined surface defining an obtuse angle (in direction of advancing count on the counter member the horizontal surface (on the non-counting side) followed by the inclined surface (on the counting side of the tooth gullet)). For those embodiments including a horizontal surface, referring to the direction of advancing count on the counter member the horizontal surface is desirably preceded by an inclined surface, such that the inclined surface and horizontal surface define an obtuse angle. Embodiments having a tooth gullet defined by at least one vertical surface on the counting side of the tooth gullet are more preferred because such a vertical surface and the ratchet member define a ratchet preventing motion of the counter member (e.g. counter ring) in the counting direction. Where present, an inclined surface on or near the non-counting side of the tooth gullet engages the ratchet member advantageously preventing motion in the non-counting direction since the counter ring is biased against the ratchet member. In the rest position of the inhaler, the trigger is typically not in engagement with the counter member, e.g. is spaced apart from the teeth of the counter member (e.g. counter ring).

In preferred embodiments of the invention the tooth apex on the counter member (e.g. counter ring) is defined between two inclined surfaces defining an obtuse, 90° or acute angle; or between a vertical surface and an inclined surface defining an acute angle (in direction of advancing count on the counter member the vertical surface is followed by the inclined surface (i.e. the vertical surface is on the non-counting side while the inclined surface is on the counting side of the tooth apex).

In the following the operation of a preferred embodiment of the dose counter for conventional press-and-breath inhalers will be described. As the aerosol container is depressed towards the firing position, downward movement of the container causes downward movement of the trigger such that it contacts an inclined surface of an upraised tooth of the counter ring near, and on the counting side of, the apex of a tooth. There is a horizontal resultant force component due to the contact angle of the trigger and associated inclined surface of the tooth but rotational motion of the counter ring is prevented due to engagement between the ratchet member and its associated tooth.

As the container and trigger are depressed further the counter ring is moved downwardly against its resilient bias e.g. by compressing the spring. During this further downward movement the ratchet member will remain engaged with the associated tooth preventing motion in the counting direction.

Further depression of the aerosol container, sufficient to cause firing of the valve causes downward movement of the trigger and counter ring to such an extent that the ratchet member becomes disengaged from the associated tooth thereby allowing rotational motion of the counter ring in the counting direction. Further depression of the aerosol container after the firing point causes further downward movement of the trigger as it acts on the inclined surface of the tooth causing rotation of the tooth until such time as the trigger member reaches the tooth gullet. At this limit of travel the counter ring will have completed the first part of its counting motion and it will have moved sufficiently such that the ratchet member is positioned over the inclined surface of the next tooth ready for engagement to the ratchet member ("next ratchet tooth").

When the aerosol container is released it returns to its rest position under the influence of the return spring of the valve, this movement will also cause an upward movement of the trigger away from the tooth of the counter ring. As the trigger moves upwardly (and eventually disengaging the tooth), the counter ring is biased upwardly against the ratchet member. During the initial upward movement of the trigger, the ratchet member engages the inclined surface of said next ratchet tooth. Under the influence of the resilient bias there is a horizontal resultant force, which causes further rotation of the counter ring in the counting direction. When the aerosol container has moved sufficiently for the metering chamber in the aerosol valve to refill, the counter ring would have moved a sufficient distance in the counting direction so that the next tooth will in positioned ready for engagement with the trigger. When the aerosol container has returned to its rest position, the ratchet member will be fully engaged within the gullet of said next ratchet tooth.

It will be appreciated that partial depression (and release) of the aerosol container, insufficient to fire the valve, will normally not result in any motion of the counter ring. After firing, if the aerosol container is partially released without returning to its rest position and then depressed, the counter ring will normally return to an intermediate position and subsequent release of the aerosol container to return to its rest position will result in the completion of the counting movement under the influence of the ratchet member. Thus, there is no double counting if there is interference with the return stroke of the trigger.

In an embodiment of the invention in which the gullet of the tooth for engagement with the ratchet member is defined by two inclined surfaces, e.g. forming an obtuse, 90° or acute angle, as the trigger moves downwardly to engage the inclined surface of the counter ring, the counter ring is depressed allowing the ratchet member to ride up an inclined surface on the counting side of the tooth gullet thereby causing rotational motion of the counter ring in the counting direction. If the aerosol container is released prior to firing, the trigger will move upwardly and the counter ring will move upwardly under the resilient bias causing the ratchet member to track down the inclined surface back to the gullet of the tooth thereby rotating the counter ring backwards to its original position.

In the previous discussion, an embodiment of the dose counter was described with reference to its use with a conventional press-and-breathe inhaler. However, it will be readily appreciated that the dose counter may be adapted for use with other devices having a reciprocal actuation means, such as dry powder inhalers, pump spray devices, and other liquid spray devices.

The counter ring conveniently counts a small number of discrete doses e.g. ten, twenty, thirty doses etc. Counting a large number of doses on a single counter ring would necessitate provision of a correspondingly larger number of teeth that would need to be smaller in order to be accommodated on the counter ring. Since most inhalers contain a greater number of doses e.g. two hundred doses, the dose counter of the invention will generally comprise a second counting ring to provide a "tens" digit or "hundreds" and "tens" digits. A third counting ring may be incorporated to count "hundreds". The second counting ring may conveniently be positioned below the main counter ring and driven such that it is advanced one unit for ten increments of the main counter ring e.g. the second counting ring is advanced each full rotation, half rotation, or third of a full rotation etc of the main counter ring depending on the number of teeth on the main counter ring. The driving may conveniently be achieved by providing internal teeth on the second counting ring which are engaged by a cog which is turned when a lug on the main counter ring intermittently engages the cog during rotations of the main counter ring.

The invention will now be described with reference to the accompanying drawings in which:

FIGS. 1A to 1H are schematic diagrams showing the principle of operation of one embodiment of a dose counter in accordance with the invention during the various stages of counting a single dose, FIG. 2 represents a schematic diagram of the principle of operation of a further dose counter in accordance with the invention, FIGS. 3A to 3D are schematic diagrams showing the principle of operation of a further dose counter in accordance with the invention, FIGS. 4A to 4D represent schematic diagrams of the principle of operation of a further dose counter in accordance with the invention, FIG. 5 represents an exploded view of a dose counter operating in accordance with the principle shown in FIGS. 1A to 1H, FIG. 6 represents a cross-section showing part of a press-and-breathe inhaler incorporating the dose counter of FIG. 5, FIG. 7 represents a counting ring suitable for use in a dose counter operating according to the principle disclosed in FIG. 3, FIG. 8 represents a counter ring for a dose counter operating in accordance with the principle disclosed in FIG. 4.

FIGS. 1A to 1H schematically illustrate the operation of a dose counter in accordance with the invention. The dose counter comprises a ratchet member (2), and trigger member (4). The counter member in the form of a ring (not shown completely) comprises two sets of teeth, a set of teeth (6) for interaction with the trigger (4) and a set of teeth (8) for interaction with the ratchet member (2).

The set of teeth (6) for engagement with the trigger (4) comprise a series of inclined surfaces (10 and 12) defining points or apices (14) and gullets (16). The set of teeth (8) for engagement with the ratchet member (2) comprise a series of inclined surfaces (18) and vertical surfaces (20) defining points or apices (24) and gullets (26). The set of teeth (6) may conveniently be positioned radially inwardly of the set of teeth (8) on the upper surface of the counter ring. Referring to FIGS. 1A to 1H, the counter member or ring rotates from right to left in two steps upon a single count or tooth. The outer surface of the counter member or ring will typically be provided with indicia or markings for the count, and thus when the counter member rotates from right to left (e.g. as shown in FIG. 1) the indicia on the outer surface counter ring will show an advancing count (which may be a count up and/or a count down) on the surface of the counter ring from left to right ("the direction of advancing count").

In the rest position shown in FIG. 1A the trigger (4) is spaced from the set of teeth (6). The fixed ratchet member (2) is engaged with a tooth (8) with the ratchet member positioned within the gullet (26). The counter ring is resiliently biased upwardly against the ratchet member (2) and rotational motion of the counter ring is prevented in one direction (from right to left, i.e. the counting direction of rotation) by engagement between the ratchet member (2) and the vertical surface (20) of the tooth (8) and in the other direction (from left to right, i.e. the non-counting direction of rotation) by engagement of an inclined surface (18) with the ratchet member (2).

As previously mentioned, the trigger member (4) may be (directly or indirectly) secured to the ferrule or the container or the valve stem of a valve, as the case may be, so that the trigger member will undergo reciprocal movement coordinated with the reciprocal movement between e.g. the valve stem of an actuation means and the container. In the following, reference is made to a conventional press-and-breath inhaler in which the valve stem is typically fixed in a nozzle of the inhaler housing and the container is depressed to cause actuation of the valve, and thus here the trigger (4) may be suitably secured to the ferrule and/or the container (not shown). FIG. 1B shows the position of the trigger member (4) during the initial stages of depression of the aerosol container to actuate the valve. Depression of the aerosol container causes downward movement of the trigger to contact the inclined surface (10) of a tooth (6).

FIG. 1C shows the position of the components after further depression of the aerosol container. The trigger (4) is further depressed causing depression of the counter ring against the resilient bias (and thus a downward movement of both sets of teeth (6,8)). Depression of the counter ring causes the inclined surface (18) of tooth (8) to separate from the ratchet member (2). Rotational motion in the counting direction is still prevented by engagement of the vertical surface (20) with the ratchet member (2).

FIG. 1D shows the position of the components at about the firing point of the valve. The trigger (4) has been further depressed causing further downward movement of the counter ring until the ratchet member (2) reaches the point of disengagement with the vertical surface (20). It will be noted that if the aerosol container is released after movement of the dose counter to the stage of FIG. 1C or up to (but not including) the point of disengagement as represented by FIG. 1D, then the counter ring will be urged vertically upwardly under the resilient bias and returned to the position of FIG. 1A.

Figure 1A:
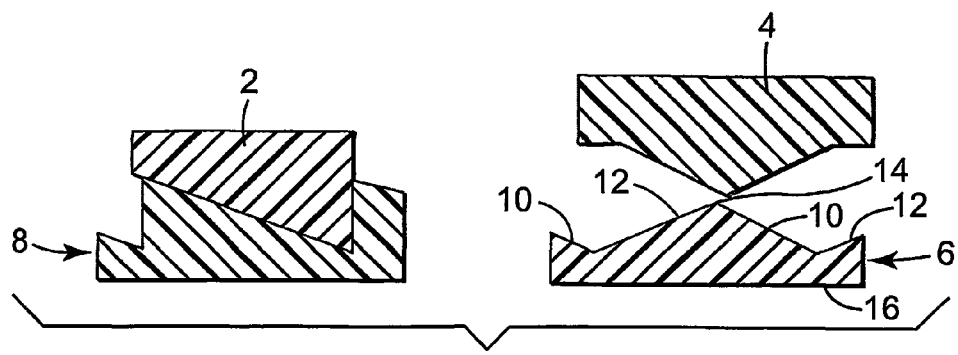
FIG. 1E shows a transitional position of the components just after firing the valve. Since motion of the counter ring is no longer blocked by the ratchet member (2), the counter ring rotates in the counting direction (from right to left) under the influence of trigger (4) pressing against the inclined surface (10).
FIG. 1F shows the limit of the travel of the counting mechanism with the trigger (4) positioned in the gullet (16) of the tooth (6). This is the position that pertains when the valve is completely compressed.
Figure 1B:
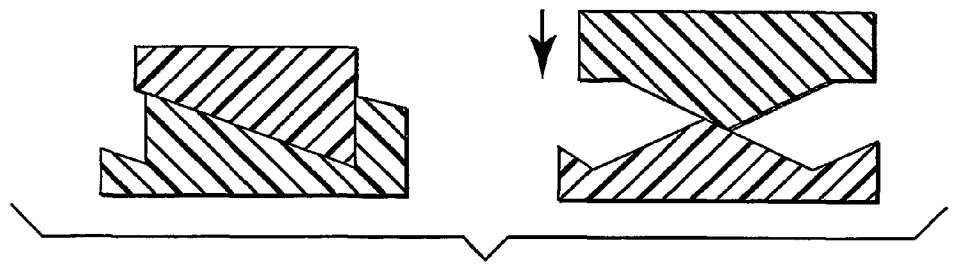
Figure 1C:
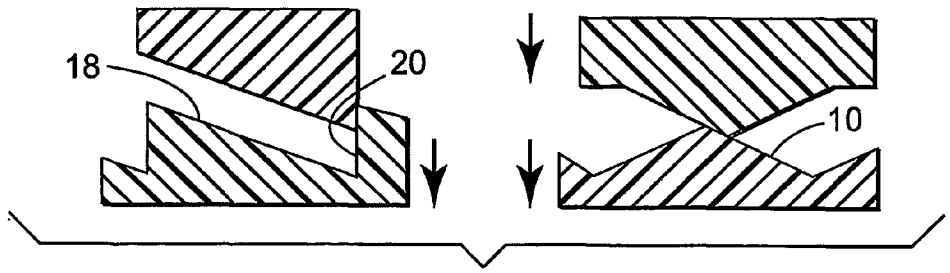
Figure 1D:
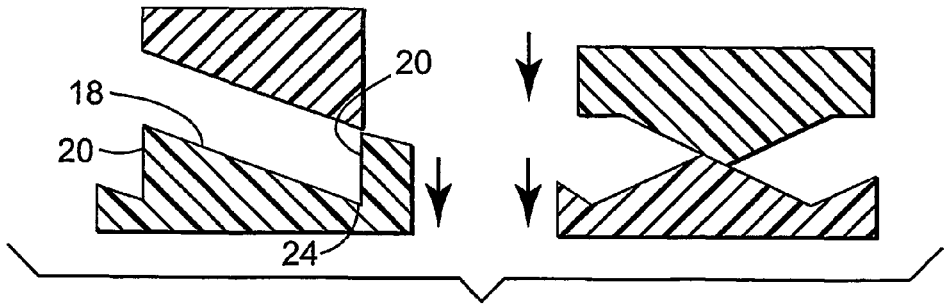
Figure 1E:
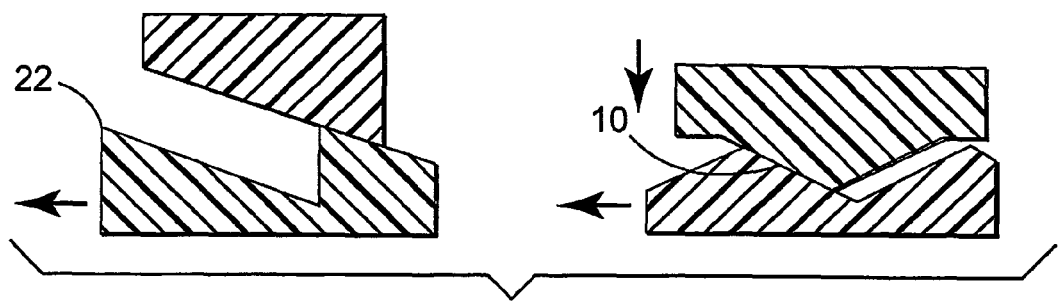
Figure 1F:
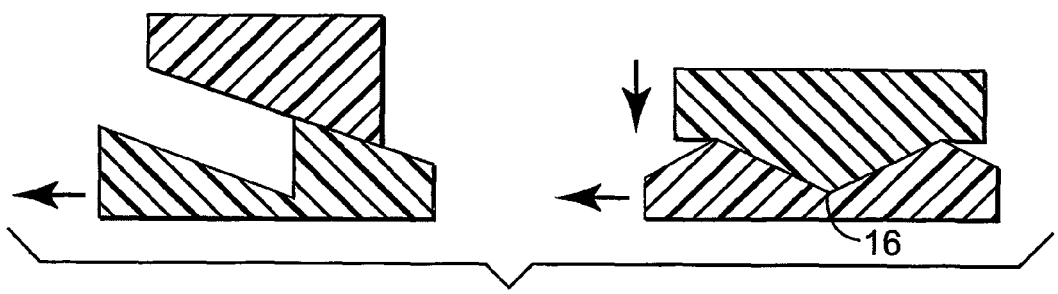
Figure 1G:
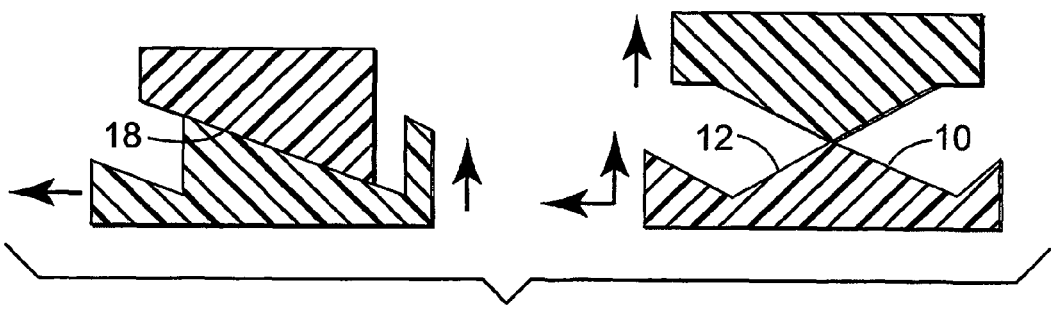

FIG. 1G shows the position of the components as the aerosol container is allowed to return towards its rest position under the influence of the return spring of the valve. As aerosol container and valve returns to its rest position, the trigger (4) moves vertically upward allowing the counter ring to move both vertically upward and in the counting direction. Vertical movement of the counting ring causes the inclined surface (18) of tooth (8) to bear against the ratchet member (2) resulting in a horizontal force component causing further rotation of the counter ring in the counting direction. The trigger (4) tracks along the inclined surface (12) until the position shown in FIG. 1G is reached, which is just prior to the point where the metering chamber of the valve will be refilled. If the aerosol container was depressed again before passing the point shown in FIG. 1G (i.e. before the trigger (4) passes over the apex (14) disengaging from the inclined surface (12)), the counting device would return to the position shown in FIG. 1F.

Figure 1H:
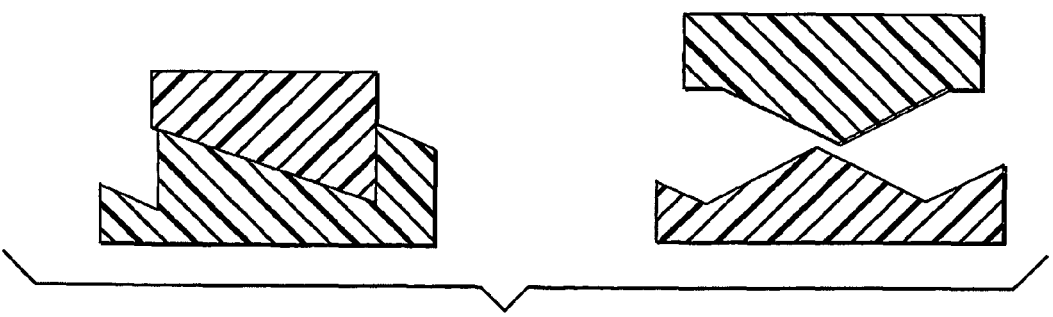

Referring to FIG. 1H, as the aerosol container is returned to the rest position, trigger (4) disengages from surface (12), and thus from the tooth (6). The counter ring continues rotation in the counting direction under the influence of a horizontal force component generated as the inclined surface (18) is urged against the ratchet member (2) until the ratchet member (2) is positioned within the gullet (26). The components have returned to the rest position shown in FIG. 1A with the counter ring advanced in the counting direction by one tooth.

As can be appreciated from the exemplary embodiment shown in FIGS. 1A to 1H, in dose counters in accordance with the invention the trigger typically moves vertically upward and downward (e.g. in a direction of reciprocal movement) in coordination with the actuator and container of the inhaler (see e.g. FIGS. 1B to 1G), while the ratchet member remains fixed relative to the rotational motion of the counter member (see e.g. FIGS. 1E to 1H). Moreover the ratchet member is typically fixed in the direction generally parallel to the direction of the counting motion of the counter member (in a direction generally orthogonal to the direction of the reciprocal movement of the trigger member), so that the counter member (e.g. counter ring) can rotate against the ratchet member. Also it can be appreciated from FIGS. 1A to 1H (in particular FIGS. 1B to 1G) that the ratchet member is also desirably fixed relative to the vertical upward and downward motion of the resiliently biased counter member. In other words, the ratchet member is desirably fixed in the direction generally normal to the direction of the counting motion of the counter member (in a direction generally parallel to the direction of the reciprocal movement of the trigger member). Referring to a conventional press-and-breath inhaler in which the trigger member is secured to the ferrule and/or the container, the ratchet member may be suitably secured (directly or indirectly) to the housing of the inhaler, e.g. by fixing the ratchet member to the housing of the dose counter which in turn is fixed to the housing of the inhaler.

Further, as can be seen in the exemplary embodiment shown in FIGS. 1A to 1H, desirably the trigger member of the dose counter is also fixed relative to the rotational motion of the counter member (see e.g. FIGS. 1E to 1H). In other words the trigger member is desirably fixed in the direction generally parallel to the direction of the counting motion of the counter member (in a direction generally orthogonal to the direction of the reciprocal movement of the trigger member).

Also as can be appreciated from the FIG. 1, dose counters in accordance with the invention desirably have a "point of no return" associated with the outward stroke of the trigger member, and more desirably two "points of no return"—one associated with the outward stroke of the trigger member and the other with the return stroke of the trigger member. Moreover, during the outward stoke of the trigger member, premature release of the aerosol container prior to the point in time in which the ratchet member just passes the next sequential apex of the counter member in the counting direction (e.g. referring to FIGS. 1D and E where the ratchet member (2) just passes over apex (24), thereby disengaging from the vertical surface (20) and engaging the subsequent inclined surface (18)) will cause the counter member to return to its rest position (e.g. as shown in FIG. 1A). Preferably this point of no return of the dose counter coincides or coincides as closely as possible to the firing of the dose by the inhaler. During the return stroke of the trigger, any additional depression of the aerosol container prior to the point in time in which the trigger just passes the next sequential apex of the counter member in the counting direction (e.g. referring to FIGS. 1G and H where the trigger (4) just passes over apex (14), thereby disengaging from the inclined surface (12)) will cause the counter member to return to an intermediate position, typically where the trigger member is engaged within a gullet (e.g. as shown in FIG. 1F). Preferably this point of no return of the dose counter associated with the return stroke of the trigger member coincides or coincides as closely as possible to the re-metering of the dose.

Figure 2:
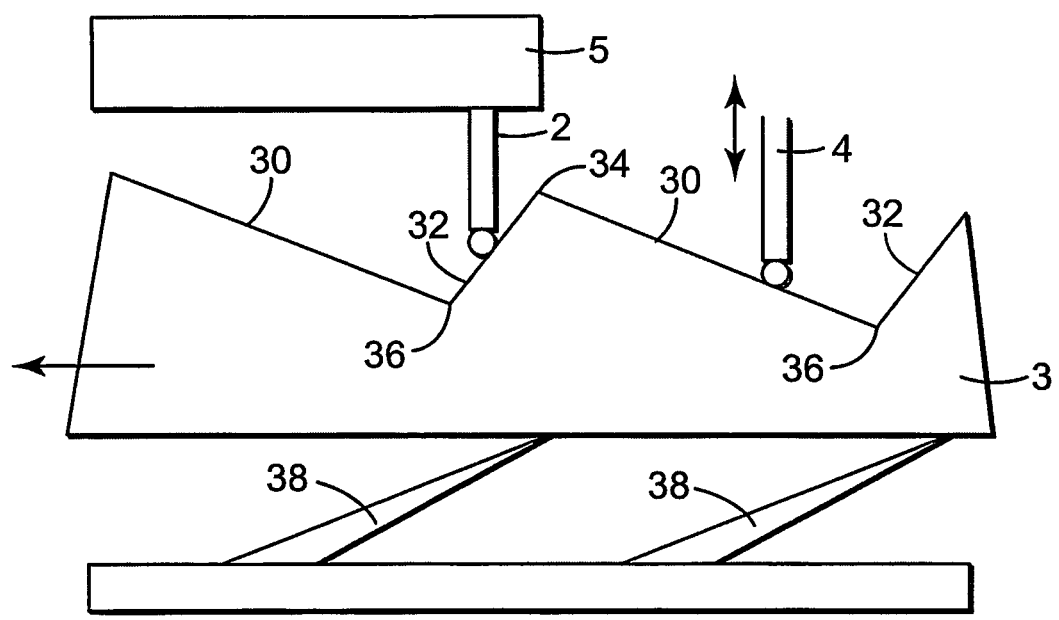

FIG. 2 is a schematic diagram showing the principle of operation of a further dose counter in accordance with the invention.

The dose counter again comprises a ratchet member (2) as well as a trigger member (4). The counter member (3), again desirably in the form of a ring (not shown completely), has a single set of teeth formed from inclined surfaces (30, 32) which define points or apices (34) and gullets (36). The counter member (3) is resiliently biased towards the ratchet member (2) e.g. by means of leaf springs (38) supported on the base (40) of a housing of the dose counter. Similarly to the previous embodiment, referring to e.g. a conventional press-and-breathe inhaler, the trigger member (4) may be indirectly or directly attached to the valve ferrule and/or aerosol container (not shown) for reciprocal movement therewith. The ratchet member (2) may be fixed to a housing (5) of the dose counter, which may in turn be fixed to a housing (not shown) of the inhaler.

As in the embodiment shown in FIG. 1, the counter member (3) will be rotated right to left in two steps upon a single count or tooth, and thus indicia (not shown) on the outer surface of the counter member will show markings for an advancing count from left to right. The dose counter schematically illustrated in FIG. 2 shows the positions of the ratchet member (2) and trigger (4) shortly after depression of the aerosol container but prior to actuation of the inhaler. Before depression and when the inhaler was at rest, the ratchet member (2) was located in first gullet (36) (the gullet to the left in the drawing) and the trigger (4) was located spaced above and just to the right of the first apex (34) (the apex to the left in the drawing). The dose counter operates as follows. For complete movement of the aerosol container to fire the valve, the trigger (4) contacts against the first inclined surface (30) of the counter member (3) and causes the counter member (3) to rotate in the counting direction (right to left) as well as pushing it down against the spring (38). Meanwhile, the ratchet member (2) is tracking up the second inclined surface (32). This embodiment is different to that disclosed in FIG. 1 in that the surface on the counting side of the tooth gullet is an inclined surface rather than a vertical surface, and thus in this embodiment, unlike that shown in FIG. 1, the tracking motion of the ratchet member (2) along the second inclined surface (32) involves a movement of the counter ring in the counting direction. As the trigger (4) is further depressed, the counter member (3) moves to a position such that the ratchet member (2) passes over the point or apex (34) in the toothed profile. As the ratchet member (2) just passes over the point or apex (34), the first point of no return, the combined effect of the spring (38) and trigger (4) then causes the counter member (3) to advance until the trigger (4) nestles in the second gullet (36') of the toothed profile.

Upon release of the aerosol container to return it to its rest position, the trigger (4) moves along the second inclined surface (32') away from the second gullet (36'), with the ratchet member (2) engaging and tracking down the first inclined surface (30). The counter member is biased against the ratchet member (2) under the influence of the spring (38) causing the counter member to rotate further in the counting direction. The trigger (4) disengages from the counter member (3) when the trigger (4) reaches the top of the second inclined surface (32') and just passes over the second point or apex (34'), the second point of no return. The combined action of the ratchet member (2) on the first inclined surface (30) and the spring (38) causes the counter member (3) to advance until the ratchet nestles in the second gullet (36') of the tooth profile. It will be appreciated that this motion beyond the second point of no return is relatively quick, depending upon the spring and the interaction of the inclined surfaces rather than any movement of the trigger.

For incomplete movement in the outward (or downward as shown in FIG. 2) stroke of the trigger (4) even where the trigger (4) has engaged the first inclined surface (30) but the ratchet member (2) has not passed over the first apex (34), i.e. has not reached the first point of no return, upon any premature release of the aerosol container and thus any subsequent return stroke of the trigger (4), the ratchet member (2) in engagement with and tracking back down the second inclined surface (32) will cause the counter member (3) to move in the direction opposite to the counting direction to restore the counter member to its rest position with the ratchet member (2) resting in the gullet (36).

For incomplete movement in the return (or upward as shown in FIG. 2) stroke of the trigger (4), prior to the trigger (4) passing over the second apex (34'), i.e. before the second point of no return, any secondary depression of the aerosol container and any secondary downward stroke of the trigger results in the trigger (4) tracking back down the second inclined surface (32') causing the counter member (3) to move in the opposite direction to the counting direction towards or back to an intermediate position wherein the trigger (4) is engaged with the second gullet (36'). Subsequent complete release of the aerosol container and thus a complete return stroke of the trigger, will allow the dose counter and counter member to complete the count and move into its rest position (i.e., with ratchet member (2) resting in the second gullet (36')).

FIG. 3A to 3D of the accompanying drawings represents schematic diagrams showing the operation of a further dose counter in accordance with the invention. The device shown in FIG. 3 is similar to the device shown in FIG. 2 in that the counter member, in the form of a ring, comprises a single ring of teeth, but in this embodiment the teeth are formed by a vertical surface and an inclined surface.

Referring to FIGS. 3A to 3D the counting device comprises a fixed ratchet member (2), a counter ring (3) resiliently biased to the ratchet member and a trigger (4) movable with the aerosol container (not shown). The counter ring (3) (not completely shown) comprises a single ring of teeth formed from inclined surfaces (30) and vertical surfaces (31) defining points (34) and gullets (36), in particular referring to the tooth apices the vertical surface (31) is on the non-counting side of each tooth apex (34) and the inclined surface (30) is on the counting side of each tooth apex (34). The small circle on the counter ring (3) represents an indicia marking.

The mode of operation is similar to that described with reference to FIGS. 1 and 2.

Figure 3A:
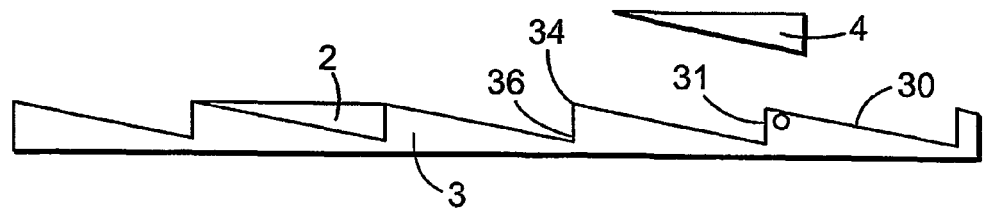

FIG. 3A shows the counter in the rest position with the ratchet member (2) fully engaged in a tooth of the counter ring (3) and the trigger member (4) spaced from the counter ring.

Figure 3B:
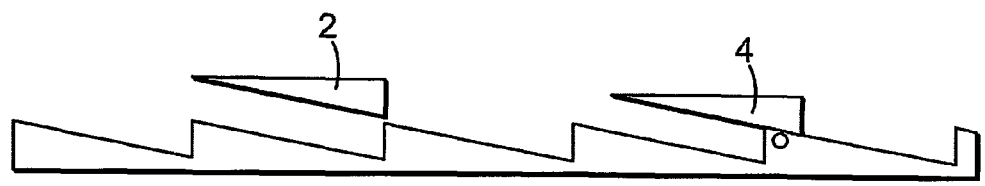

FIG. 3B shows the counter at a transitional position, typically corresponding to the firing position of the valve, where the counter member (3) is depressed to such an extent through the trigger (4) pressing against the inclined surface (30) that the ratchet member (2) has just passed over apex (34), i.e., just past the first point of no return, and disengaged from the vertical surface (31) of a tooth.

Figure 3C:
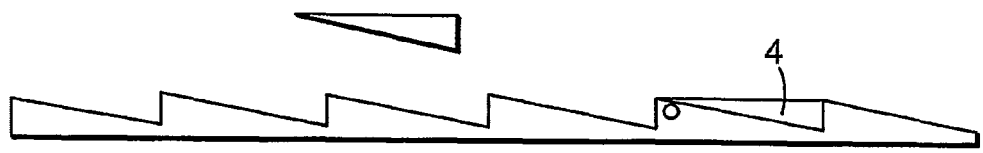

FIG. 3C shows the counter, at a position corresponding to full extent of travel of the valve stem of an actuation means (e.g. valve) of the inhaler, where the trigger (4) is also at a position of full extent of travel with the trigger fully engaged in a tooth.

Figure 3D:
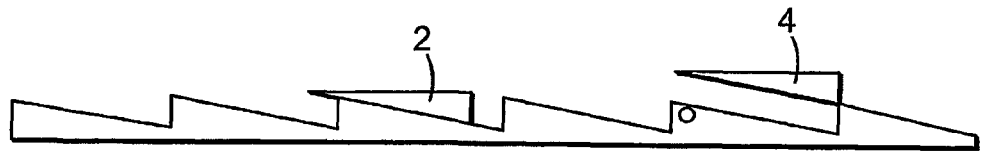

FIG. 3D shows the counter just prior to the second point of no return, typically corresponding to the re-metering position of the valve. The trigger (4) is about to pass over the apex (34) and disengage from the vertical surface (31) of a tooth. The counter member (3) has been urged in contact with the ratchet member (2) under the influence of the biasing means. As the aerosol container returns to its rest position and the trigger (4) passes over the apex (34), the dose counter will return (by rotating further from right to left) to its rest position (e.g. as shown in FIG. 3A with the counter ring advanced by one tooth).

For dose counters having one set of teeth on the counter member, the pitch of the teeth is determined by the size of any numbers or markings to be printed on the ring and the desire to have a round number of teeth (e.g. twenty or another factor of 10) to fit the circumference of the ring. The amplitude of teeth is determined largely by the distance corresponding to the difference in valve stem displacement during the actuation of the valve, e.g. between re-metering and firing of the dose. The angle of the first inclined surface (in reference to the teeth apices, the first inclined surface is understood to be that inclined surface to the counting side of each tooth apex, e.g. the inclined surfaces marked with the reference number 30 in FIGS. 2 and 3) needs to be steep enough to allow the ring to be advanced by relative motion with the trigger or ratchet, but must not be too steep to allow the required dimensions of pitch and amplitude to be satisfied. The angle on the second inclined or vertical surface (in reference to the teeth apices, the second inclined surface or vertical surface is understood to be that inclined or vertical surface to the non-counting side of each tooth apex, e.g. the surfaces marked with the reference numbers 31 and 32 in FIGS. 2 and 3) is not essential in regard to advancement of the counter ring. For example, because a vertical surface will prevent advancement of the ring until the point of no return is reached, no reverse movement would be necessary to return it if movement is incomplete. The first inclined surface typically needs to have a projected length on the circumference of the ring that is greater than the corresponding distance separation between trigger and ratchet members, which in turn is typically greater than the corresponding projection of the second inclined surface. This allows the trigger and ratchet to straddle the second inclined surface, but not the first inclined surface.

One possible way of increasing the angle of the inclined surface is to increase the number of teeth on the ring. However, there is a limit to the number of teeth on each ring and to the number of indicia that can be printed on the outside of the ring in a manner that is clearly visible to the user. An alternative way of increasing the slope of the inclined surface is to alter the profile of the teeth to provide a flat region between teeth, in particular a flat or horizontal region in the gullet of the teeth. The profile of the ratchet member and/or trigger may be configured to conform to the profile of the respective teeth of the counter member.

FIGS. 4A to 4D show the principles of operation of a further embodiment of a dose counter in accordance with the invention. The dose counter is similar to that described with respect to FIGS. 1A to 1H with the exception that each tooth in the set of teeth (8) for co-operation with the ratchet member (2) has a profile defined—in the direction of advancing count on the counter member or ring—by an inclined surface (18), a horizontal surface or a flattened surface (21) and a vertical surface (20). The gullet of a tooth (26) is defined between the horizontal or flattened surface (21) and vertical surface (20).

The mode of operation of the dose counter is identical to the dose counter illustrated in FIGS. 1A to 1H.

Figure 4A:
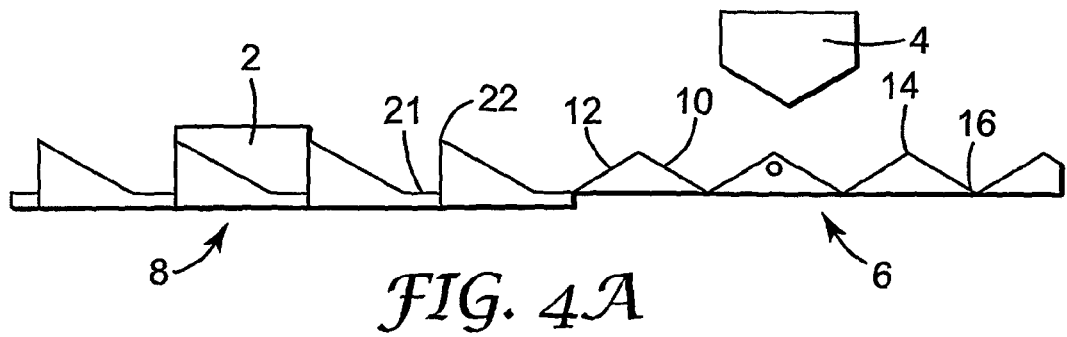
Figure 4B:
Figure 4C:
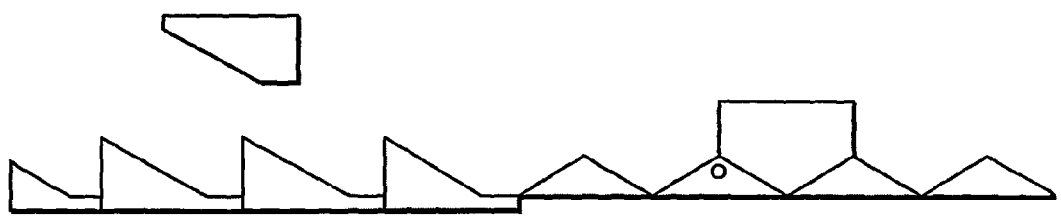
Figure 4D:
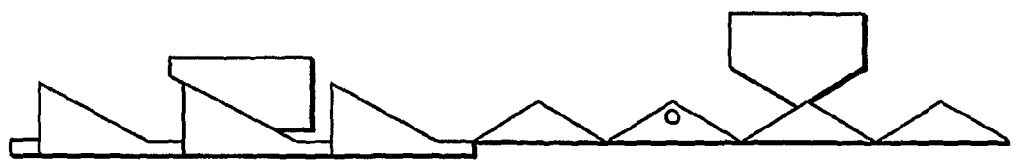

FIG. 4A represents the dose counter in its rest position, FIG. 4B represents the position of the dose counter at about the firing of the valve of the inhaler, FIG. 4C represents the dose counter at the full extent of travel of the trigger member (4) and FIG. 4D represents the position of the dose counter at about the re-metering position of the valve.

Figure 5:
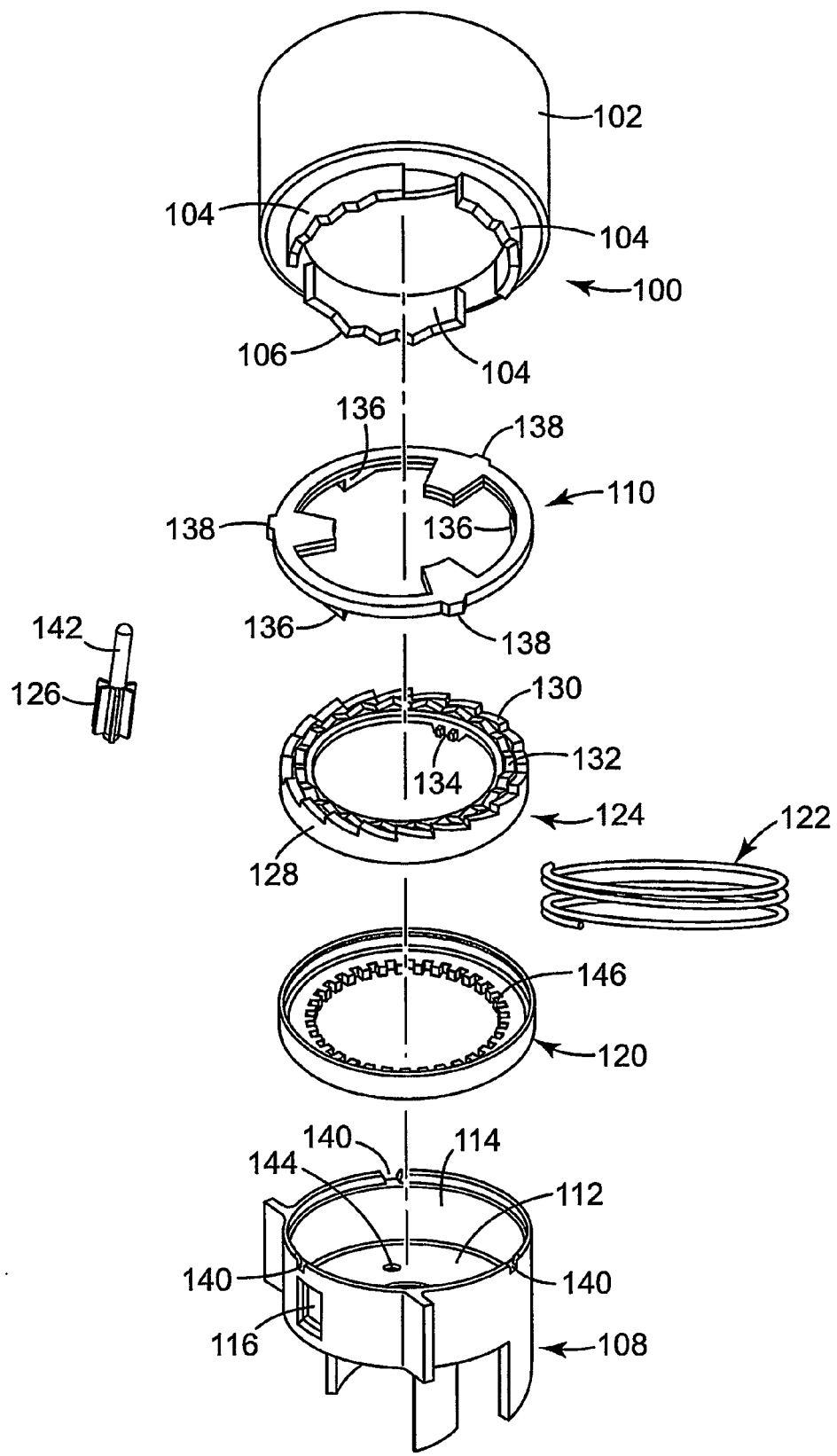

FIG. 5 of the accompanying drawings represents an exploded view of a dose counter of the invention which operates on the principles illustrated in FIGS. 1A to 1H.

The dose counter comprises a trigger portion (100) having a cylindrical skirt (102) that is dimensioned to provide a force fit around the ferrule of the valve of an aerosol inhaler. The trigger portion (100) has three sections (104) of downwardly extending teeth or trigger members (106), which are configured to correspond to teeth (132) on the counter ring (124). The trigger portion (100) and thus the teeth or trigger members (106) will move with the aerosol container and valve ferrule to which it is affixed.

The dose counter comprises a housing consisting of a lower portion (108) and a lid (110). The lower portion (108) comprises a base (112) and a cylindrical sidewall (114). The sidewall (114) includes a window (116) through which the markings on the counter ring (124) and counting ring (120) may be viewed, although this may not be required if the lower portion is made of a transparent material. The lower portion is provided with feet (145) to locate into the aerosol actuator, as partly shown in FIG. 6, and may be held in place by having these components designed to snap-fit.

The housing accommodates a "tens" counting ring (120), spring (122), counter ring (124) and cog (126).

Counter ring (124) comprises a cylindrical sidewall (128) upon which the appropriate markings or indicia (not shown) are printed. On its upper surface the counter ring (124) comprises two rings of upstanding teeth. The outer ring of teeth (130) for engagement with the ratchet members (136) correspond to the teeth (8) in FIG. 1. The inner ring of teeth (132) for engagement with the triggers or trigger members (106) correspond to the teeth (6) in FIG. 1. The counter ring (124) additionally comprises two sets of lugs (134) positioned diametrically opposite each other projecting radially inwardly from the interior of the counter ring. The lugs are for engagement with the cog (126), the function of which will be described hereinafter.

The housing lid (110) comprises three fixed ratchet members (136) which extend downwardly from the lid. The ratchet members (136) are configured to mate with the outer ring of teeth (130) on the counter ring (124), as shown and described in FIG. 1 (for ratchet members (2) mating with teeth (8)). The lid (110) may be firmly secured to the lower portion of the housing (108) by projections (138) that provide a snap-fit connection within recesses (140) of the lower portion (108), or may be a press-fit or may be ultrasonically welded onto the lower portion.

Cog (126) comprises an axle (142) that is mounted for rotation with one end in an aperture (144) in the base (112) of the housing and the other end located in a corresponding aperture on the lid (not shown). The teeth of the cog (126) engage with a radially inwardly projecting ring of teeth (146) on the "tens" counting ring (120).

Figure 6:
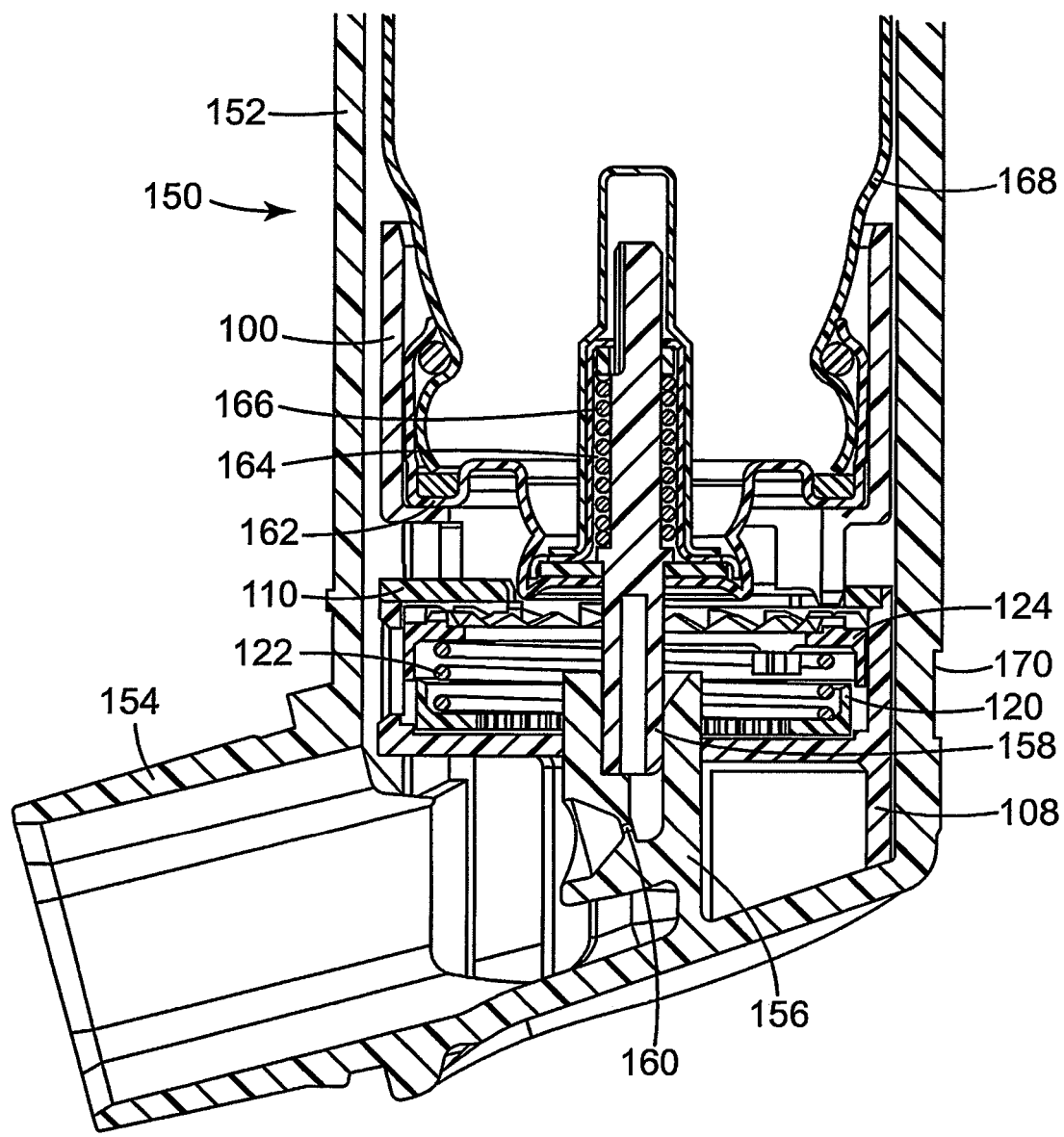

FIG. 6 shows a vertical cross-sectional view through part of a press-and-breathe aerosol inhaler incorporating the dose counter of FIG. 5. The display may indicate the number of doses remaining or the number dispensed. The indicia may be suitably alphabetic, numerical, alphanumeric, or colour symbols, providing a sequential count-up or count-down of dispensed doses or providing a more general indication such as "Full" or "Empty". The indicia may be visible through a window (170) in the actuator's cylindrical sidewall; alternatively, the sidewall may have at least a portion made of a transparent material. The press-and-breathe inhaler comprises a housing (150) having a cylindrical body (152-points to the can in the figure) to accommodate the aerosol container (168) and a mouthpiece (154). A nozzle block (156) is positioned within the housing having an aperture to accommodate the valve stem (158) and a spray orifice (160).

The metering valve of the aerosol container comprises a valve ferrule (162), valve stem (158), metering chamber (164) and return spring (166).

The parts of the dose counter are labelled with the same reference numerals as in FIG. 5.

The mode of operation of the dose counter illustrated in FIGS. 5 and 6 is described in detail with reference to FIG. 1. As each dose is dispensed the counter ring (124) will advance by one increment (one tooth) and the appropriate dose may be viewed through the viewing window (170). The "tens" counting ring (120) will remain stationary until such time as the counter wheel (124) has rotated sufficiently for lugs (134) to engage the cog wheel (126). Further rotation of the counter ring (124) causes the cog (126) to rotate causing corresponding transient rotation of the "tens" counting ring (120). Thereafter, the "tens" counting ring will only rotate again when the counter ring has rotated nearly a further 180° i.e. the "tens" ring will only move every ten doses if the counter ring has twenty teeth. Whilst the "tens" counting ring may have a smaller diameter than the counter ring, it may be preferable to have the "tens" counting ring larger in diameter, as illustrated in FIG. 6. This allows more space to provide 2 digits on the outer surface of the "tens" counting ring. Additionally, the "tens" ring could incorporate an upwardly extending shroud to cover the display of the "units" ring upon reaching the "empty" count indication. Further doses dispensed beyond this point would not change the displayed indication, which would be whatever is printed on the "tens" counting ring.

It may furthermore be desirable to incorporate an alternative air inlet into the actuator to compensate for any slight obstruction of airflow due to the counter assembly. This may be achieved by forming a series of parallel slots in the base of the actuator.

Figure 7:
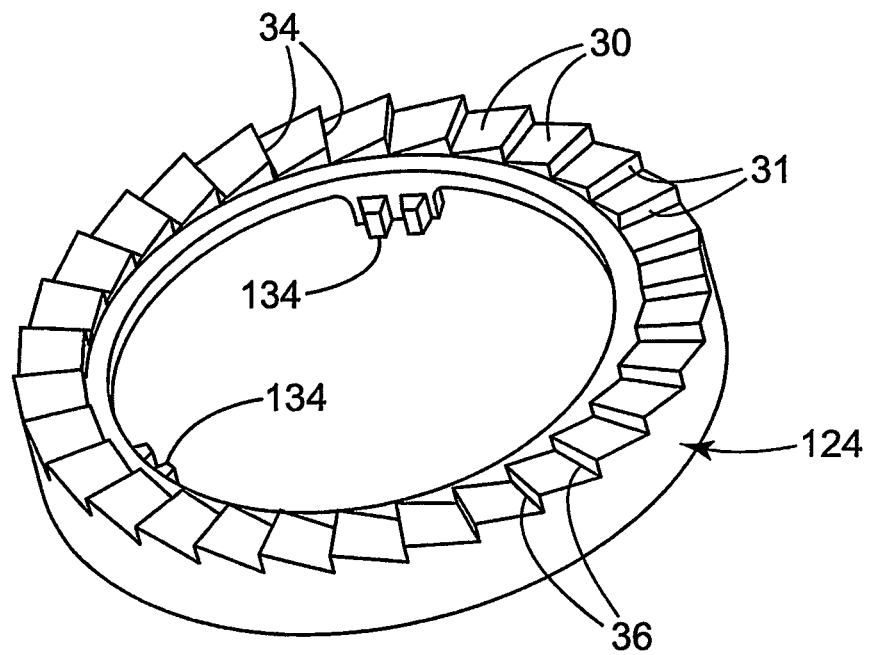

FIG. 7 of the accompanying drawings illustrates a counter ring (124) for a dose counter which operates in accordance with the principles described with reference to FIG. 3. The counter ring (124) comprises a single set of teeth defined by inclined surfaces (30) and vertical surfaces (31) forming points or apices (34) and gullets (36).

The constructions of the dose counter is otherwise identical to that disclosed in FIGS. 5 and 6 with the exception that the teeth (106) of the trigger portion (100) and the ratchet members (136) of the lid (110) will be configured to conform with the teeth on the counter ring. Also, since the counter ring comprises thirty teeth, there are three sets of lugs (134) for co-operation with the cog (126) to index the "tens" ring (120).

Figure 8:
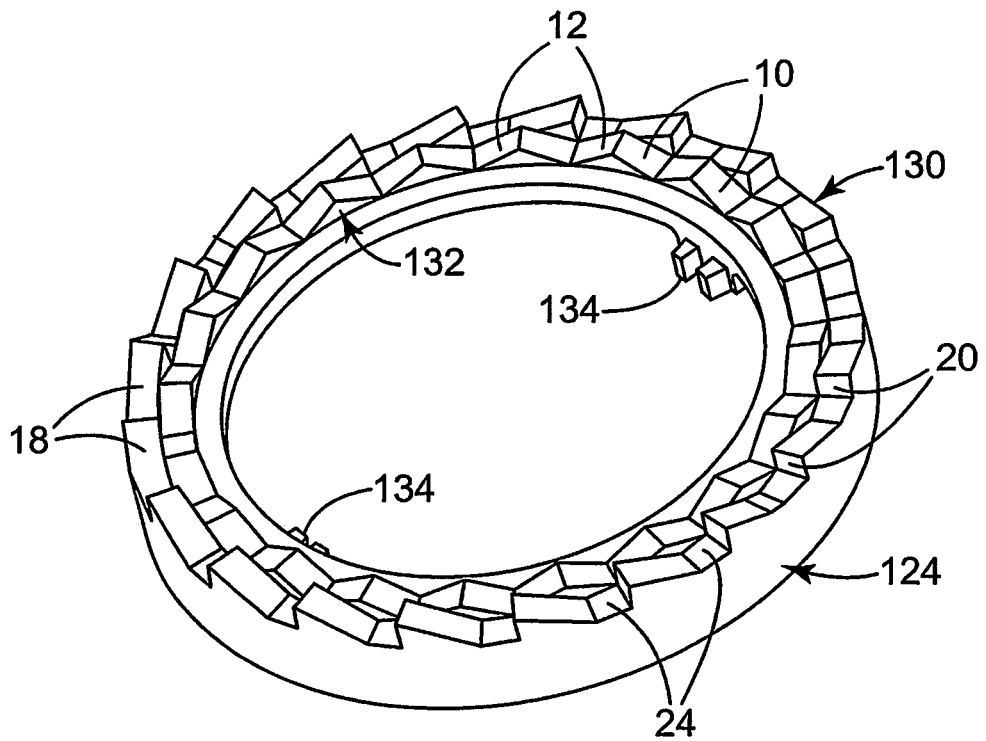

FIG. 8 of the accompanying drawings illustrates a counter ring used in a dose counter which operates in accordance with the principles described in FIG. 4. The counter ring (124) comprises an outer ring of teeth (130) and an inner ring of teeth (132), each ring having twenty teeth.

The outer ring of teeth (130) comprises inclined surfaces (18), vertical surfaces (20) and horizontal surfaces or flat regions (21). The inner ring of teeth (132) comprises inclined surfaces (10 and 12).

The remainder of the dose counter is identical to that disclosed with reference to FIGS. 5 and 6 with the exception that the ratchet members (136) on the lid (110) are configured to mate with the teeth of the outer ring (130). The ring (124) comprises two sets of lugs (134), diametrically opposed, for co-operation with the cog (126) to index the "tens" ring.

The invention claimed is:

1. A dose counter for use with an inhaler comprising a container for medicament equipped with a reciprocal actuator to dispense a dose of medicament therefrom, the dose counter comprising:
   a fixed ratchet member,
   a trigger member constructed and arranged to undergo reciprocal movement co-ordinated with the reciprocal movement between the actuator and the container, said reciprocal movement comprising an outward stroke and a return stroke,
   a counter member in the form of a ring comprising inclined surfaces in the form of at least one set of teeth constructed and arranged to undergo a predetermined counting movement each time a dose is dispensed, the counter member being biased in one direction towards the ratchet and trigger members and being capable of counting motion in a direction generally orthogonal to the direction of reciprocal movement of the trigger, the counter member comprising:
   a first region for interaction with the trigger which comprises at least one inclined surface which is engaged by the trigger during its outward stroke causing the counter member to undergo counting motion,
   a second region for interaction with the ratchet member which comprises at least one inclined surface which is engaged by the ratchet member during the return stroke of the trigger causing the counter member to undergo further counting motion to complete said predetermined counting movement.

2. A dose counter as claimed claim 1 in which the ring comprises one set of teeth to interact with the trigger and a second set of teeth to interact with the ratchet member.

3. A dose counter as claimed in claim 1 in which the ring comprises a single set of teeth which interact with both the trigger and the ratchet member.

4. A dose counter as claimed in claim 2 in which there is a flat region between adjacent teeth.

5. A dose counter according to claim 1 in which the first region of interaction is longer than the second region of interaction.

6. A dose counter according to claim 1 in which an incomplete part of the counting motion associated with the first region of interaction followed by reverse movement of the trigger does not result in a net counting motion.

7. A dose counter according to claim 1 in which an incomplete part of the counting motion associated with the second region of interaction followed by reverse movement of the trigger does not result in counting motion beyond said predetermined counting movement.

8. A dose counter according to claim 1 which comprises a second counting ring which undergoes counting motion in response to counting movement of the counter ring.

9. A dose counter as claimed in claim 1 which comprises a housing to accommodate the counter member, said ratchet member being fixed to the housing.

10. An inhaler incorporating a dose counter as defined in claim 1.

11. An inhaler as claimed in claim 10, in which the container of the inhaler contains a medicinal aerosol formulation.

12. An inhaler as claimed in claim 10 in which the trigger is attached to the inhaler canister and/or valve ferrule.

* * * * *

UNITED STATES PATENT AND TRADEMARK OFFICE
CERTIFICATE OF CORRECTION

PATENT NO. : 8,740,014 B2
APPLICATION NO. : 10/596325
DATED : June 3, 2014
INVENTOR(S) : Graham Purkins Page 1 of 1

It is certified that error appears in the above-identified patent and that said Letters Patent is hereby corrected as shown below:

Title page, Column 2, item [57] (Abstract)
Line 5-6, Delete "coordinated" and insert -- co-ordinated --, therefor.

In the Specification

Column 4
Line 50, Delete "and or" and insert -- and/or --, therefor.
Line 65, After "90°" insert -- or acute angle; --.

Column 7
Line 1, Delete "etc" and insert -- etc. --, therefor.

Column 11
Line 36, Delete "FIG." and insert -- FIGS. --, therefor.

In the Claims

Column 16
Line 1, Claim 2, after "claimed" insert -- in --.

Signed and Sealed this
Third Day of March, 2015

Michelle K. Lee
*Deputy Director of the United States Patent and Trademark Office*